United States Patent
Sagehashi et al.

(10) Patent No.: US 8,686,166 B2
(45) Date of Patent: Apr. 1, 2014

(54) PREPARATION OF 2,2-BIS (FLUOROALKYL) OXIRANE AND PREPARATION OF PHOTOACID GENERATOR THEREFROM

(75) Inventors: Masayoshi Sagehashi, Joetsu (JP); Takeru Watanabe, Joetsu (JP); Youichi Ohsawa, Joetsu (JP); Koji Hasegawa, Joetsu (JP); Masaki Ohashi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/526,569

(22) Filed: Jun. 19, 2012

(65) Prior Publication Data
US 2013/0005997 A1 Jan. 3, 2013

(30) Foreign Application Priority Data
Jun. 29, 2011 (JP) ................................. 2011-144456

(51) Int. Cl.
C07D 301/27 (2006.01)
C07D 301/02 (2006.01)
C07C 69/74 (2006.01)
C07C 309/00 (2006.01)

(52) U.S. Cl.
USPC ............ 549/518; 549/514; 560/116; 562/108

(58) Field of Classification Search
USPC ................... 549/518, 514; 562/108; 560/116
See application file for complete search history.

(56) References Cited

U.S. PATENT DOCUMENTS

| | | | |
|---|---|---|---|
| 4,297,287 A | 10/1981 | Costantini et al. | |
| 4,853,378 A | 8/1989 | Hamma et al. | |
| 5,120,866 A | 6/1992 | Castellan et al. | |
| 6,653,419 B1 | 11/2003 | Petrov et al. | |
| 7,511,169 B2 | 3/2009 | Ohsawa et al. | |
| 7,868,199 B2 | 1/2011 | Hasegawa et al. | |
| 2004/0162321 A1 | 8/2004 | Kuzmich et al. | |
| 2005/0131241 A1 | 6/2005 | Song et al. | |
| 2008/0177097 A1 | 7/2008 | Petrov | |
| 2010/0209827 A1 | 8/2010 | Ohashi et al. | |

FOREIGN PATENT DOCUMENTS

| | | |
|---|---|---|
| EP | 0 473 547 A1 | 3/1992 |
| JP | 53-119805 A | 10/1978 |
| JP | 62-53978 A | 3/1987 |
| JP | 63-264452 A | 11/1988 |
| JP | 4-230645 A | 8/1992 |
| JP | 2005-84365 A | 3/2005 |
| JP | 2006-516256 A | 6/2006 |
| JP | 2007-509069 A | 4/2007 |
| JP | 2007-145797 A | 6/2007 |
| JP | 2007-204385 A | 8/2007 |
| JP | 2007-291010 A | 11/2007 |
| JP | 2009-235037 A | 10/2009 |
| JP | 2010-215608 A | 9/2010 |

OTHER PUBLICATIONS

Petrov, "Reactions of 2, 2-bis(trifluoromethyl) oxirane with alcohols under phase transfer catalysis", Journal of Flourine Chemistry, vol. 125, 2004, pp. 531-536.
Djakovitch, L. et al, "Rearrangements of Phenylthio Substituted 1,n-Diols with Toluene-p-sulfonic Acid and with Toluene-p-sulfonyl Chloride," Tetrahedron Letters, 1995, vol. 36, No. 10, pp. 1723-1726.
Larock, R.C. et al, "Comprehensive organic transformations: a guide to functional group preparations," 2nd ed., 1999, pp. 898-900.
Mischitz, M. et al, "Asymmetric Microbial Hydrolysis of Epoxides," Tetrahedron: Asymmetry, 1995, vol. 6, No. 6, pp. 1261-1272.

*Primary Examiner* — Taylor Victor Oh
(74) *Attorney, Agent, or Firm* — Birch, Stewart, Kolasch & Birch, LLP

(57) ABSTRACT

A 2,2-bis(fluoroalkyl)oxirane (A) is prepared by reacting a fluorinated alcohol (1) with a chlorinating, brominating or sulfonylating agent under basic conditions to form an oxirane precursor (2) and subjecting the oxirane precursor to ring closure under basic conditions. $R^1$ and $R^2$ are fluoroalkyl groups, $R^3$ and $R^4$ are hydrogen or monovalent hydrocarbon groups, X is chlorine, bromine or $-OSO_2R^5$ group, and $R^5$ is alkyl or aryl.

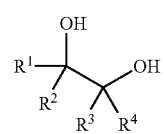

(1)

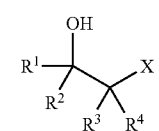

(2)

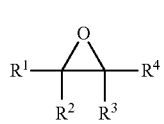

(A)

3 Claims, No Drawings

PREPARATION OF 2,2-BIS (FLUOROALKYL) OXIRANE AND PREPARATION OF PHOTOACID GENERATOR THEREFROM

CROSS-REFERENCE TO RELATED APPLICATION

This non-provisional application claims priority under 35 U.S.C. §119(a) on Patent Application No. 2011-144456 filed in Japan on Jun. 29, 2011, the entire contents of which are hereby incorporated by reference.

TECHNICAL FIELD

This invention relates to a novel method for preparing 2,2-bis(fluoroalkyl)oxiranes and a method for preparing photoacid generators therefrom.

BACKGROUND ART 2,2-Bis(fluoroalkyl)oxiranes such as 2,2-bis(trifluoromethyl)oxirane are partially fluorinated oxirane compounds. Since these oxiranes are susceptible to ring opening using various nucleophilic reagents, they are regarded promising in the field of photolithography or the like as a building block for fluoroalcohol skeleton as indicated in Patent Documents 1 and 2.

In the industry, these oxiranes are prepared by oxidation of fluorinated olefins. The direct oxidation method of reacting fluorinated olefins with oxygen is known from Patent Documents 1 and 3. Reaction with a metal hypochlorite as an oxidizing agent in the presence of a phase transfer catalyst is reported in Patent Document 2 and Non-Patent Document 1. In either method, the starting reactant or fluorinated olefin, which is gaseous, is difficult to handle and leaves concern about harm by vapor inhalation. In the direct oxidation method, toxic by-products such as hexafluoroacetone form. With respect to handling of the starting fluorinated olefins and the by-products which are gas or low-boiling liquid, a plant for large volume synthesis may be modified so as to ensure safe reaction. In the case of middle to small scale systems, typically multi-purpose reactors, however, the safety measure is uncertain and problems are left.

The foregoing oxiranes find a typical application as photoacid generators in the photolithography. Patent Document 4 describes that triphenylsulfonium 2-acyloxy-3,3,3-trifluoromethyl-2-trifluoromethylpropanesulfonate is prepared by starting with 2,2-bis(trifluoromethyl)oxirane and effecting ring-opening reaction with a hydrogensulfite. For a safe and consistent supply of the oxiranes which are useful reactants for such photoresist components, a method capable of readily preparing the oxiranes is desired.

CITATION LIST

Patent Document 1: US 20080177097
Patent Document 2: U.S. Pat. No. 6,653,419
Patent Document 3: JP-A S62-53978
Patent Document 4: JP-A 2010-215608 (US 20100209827)
Non-Patent Document 1: Journal of Fluorine Chemistry Vol. 125, p 531 (2004)

DISCLOSURE OF INVENTION

An object of the invention is to prepare a 2,2-bis(fluoroalkyl)oxirane in a simple and safe way to ensure a consistent supply thereof. Another object is to provide a method of preparing an onium salt type photoacid generator for use in the photolithography by using the resulting oxirane as the starting reactant.

The inventors have found that a 2,2-bis(fluoroalkyl)oxirane can be readily prepared in high yields using a starting reactant which is easy to handle, and that an onium salt type photoacid generator can be prepared using the resulting oxirane.

In one aspect, the invention provides a method for preparing a 2,2-bis(fluoroalkyl)oxirane having the general formula (A), comprising the steps of reacting a fluorinated alcohol having the general formula (1) with a chlorinating agent, brominating agent or sulfonylating agent under basic conditions to form an oxirane precursor having the general formula (2), and subjecting the oxirane precursor to ring closure under basic conditions.

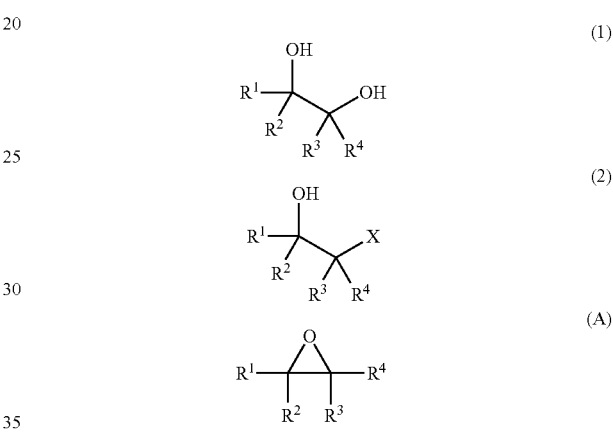

Herein $R^1$ and $R^2$ are each independently a $C_1$-$C_6$ straight or branched fluoroalkyl group, $R^3$ and $R^4$ are each independently hydrogen or a $C_1$-$C_{15}$ straight, branched or cyclic monovalent hydrocarbon group, or $R^3$ and $R^4$ may bond together to form a ring with the carbon atom to which they are attached, X is chlorine, bromine or —$OSO_2R^5$ group, and $R^5$ is a $C_1$-$C_{15}$ straight, branched or cyclic alkyl group or an aryl group which may contain a heteroatom.

In another aspect, the invention provides a method for preparing a sulfonic acid salt compound having the general formula (3), comprising the step of reacting the 2,2-bis(fluoroalkyl)oxirane having the general formula (A) prepared as above with a sulfur compound.

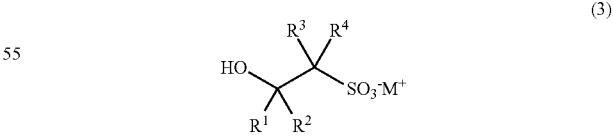

Herein $R^1$ to $R^4$ are as defined above, and M is a cation.

In a further aspect, the invention provides a method for preparing a sulfonium or iodonium salt compound having the general formula (4a) or (4b), comprising the step of subjecting the sulfonic acid salt compound having the general formula (3) prepared as above to ion exchange reaction with a sulfonium salt or iodonium salt and acylation reaction.

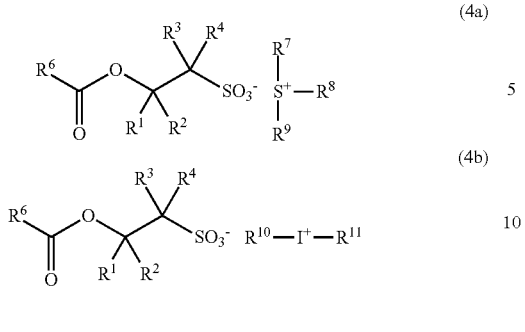

(4a)

(4b)

Herein $R^1$ to $R^4$ are as defined above, $R^6$ is a $C_1$-$C_{50}$ straight, branched or cyclic monovalent hydrocarbon group which may contain a heteroatom, $R^7$, $R^8$ and $R^9$ are each independently a $C_1$-$C_{10}$ straight or branched alkyl, alkenyl or oxoalkenyl group which may contain a fluorine atom, hydroxyl group or ether bond, or a substituted or unsubstituted $C_6$-$C_{18}$ aryl, aralkyl or aryloxoalkyl group, or any two or more of $R^7$, $R^8$ and $R^9$ may bond together to form a ring with the sulfur atom, $R^{10}$ and $R^{11}$ are each independently a substituted or unsubstituted $C_6$-$C_{18}$ aryl, aralkyl or aryloxoalkyl group, or $R^{10}$ and $R^{11}$ may bond together to form a ring with the iodine atom.

ADVANTAGEOUS EFFECTS OF INVENTION

According to the method of the invention, 2,2-bis(fluoroalkyl)oxiranes can be readily prepared using starting reactants which are easy to handle, rather than the fluorinated olefins which are gaseous, potentially harmful upon vapor inhalation, and difficult to handle. The method may use an ordinary production system rather than the special production system intended to use gaseous reactants and is applicable on a variety of production scales. The method entails no toxic by-products and is very useful in the industry. The overall process involving preparation of oxiranes and preparation of onium salt photoacid generators may be consecutively carried out without resorting to the prior art oxirane supply method.

DESCRIPTION OF EMBODIMENTS

As used herein, the terminology "($C_x$-$C_y$)" as applied to a particular unit means having a carbon atom content of from "x" carbon atoms to "y" carbon atoms per such unit.

Making investigations in order to ensure a safe and consistent supply of 2,2-bis(fluoroalkyl)oxiranes as the useful reactant for photoresist components, the inventors have succeeded in preparing a 2,2-bis(fluoroalkyl)oxirane of the general formula (A) by using a compound of the general formula (1) as the starting reactant and effecting reaction via an intermediate compound of the general formula (2). Only the compounds which are easy to handle are used, rather than the reactants which are gaseous, potentially harmful upon vapor inhalation, and difficult to handle. Eventually the inventors have succeeded in establishing an overall process that proceeds from preparation of oxiranes to preparation of onium salt photoacid generators using the resulting oxiranes in a consistent manner.

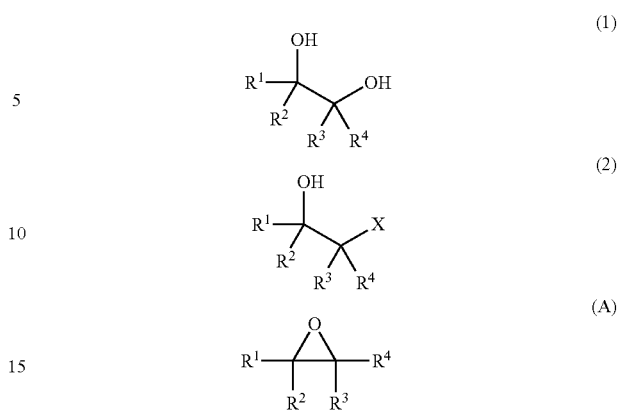

(1)

(2)

(A)

Herein $R^1$ and $R^2$ are each independently a $C_1$-$C_6$ straight or branched fluoroalkyl group. $R^3$ and $R^4$ are each independently hydrogen or a $C_1$-$C_{15}$ straight, branched or cyclic monovalent hydrocarbon group, or $R^3$ and $R^4$ may bond together to form a ring with the carbon atom to which they are attached. X is a chlorine atom, bromine atom or —$OSO_2R^5$ group wherein $R^5$ is a $C_1$-$C_{15}$ straight, branched or cyclic alkyl group or an aryl group which may contain a heteroatom.

Suitable $C_1$-$C_6$ straight or branched fluoroalkyl groups represented by $R^1$ and $R^2$ include the following, but are not limited thereto.

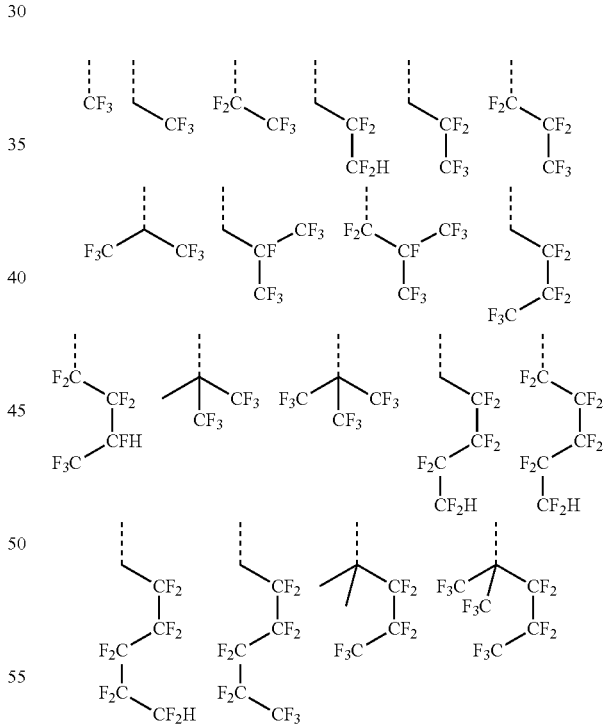

Herein and throughout the disclosure, the broken line denotes a valence bond.

Of these, $R^1$ and $R^2$ are most preferably trifluoromethyl.

Suitable $C_1$-$C_{15}$ straight, branched or cyclic monovalent hydrocarbon groups represented by $R^3$ and $R^4$ include, but are not limited to, methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl. When R$^3$ and R$^4$ bond together to form a ring, suitable rings include the following structures, but are not limited thereto.

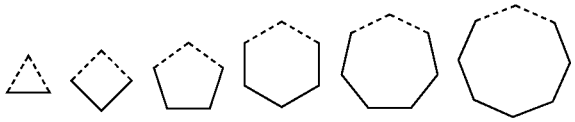

Of these, R$^3$ and R$^4$ are most preferably hydrogen.

In formula (2), X may be —OSO$_2$R$^5$ group wherein R$^5$ is a C$_1$-C$_{15}$ straight, branched or cyclic alkyl group or an aryl group each optionally substituted with a heteroatom. Suitable alkyl and aryl groups represented by R$^5$ include the following, but are not limited thereto.

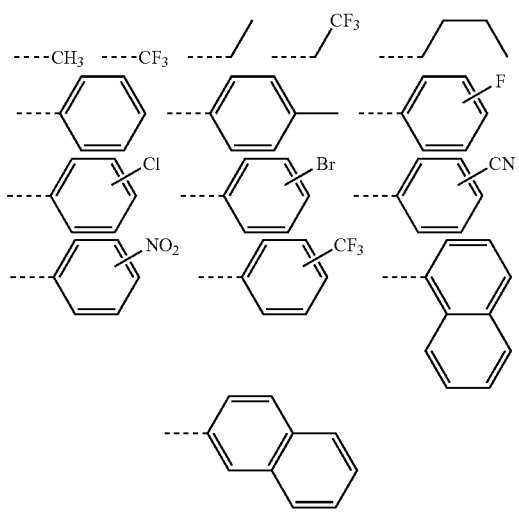

Of these, R$^5$ is most preferably 4-tolyl.

Below the methods of preparing 2,2-bis(fluoroalkyl)-oxiranes and onium salt photoacid generators are described in detail.

The first embodiment of the invention is a method for preparing a 2,2-bis(fluoroalkyl)oxirane (A), which starts with a fluorinated alcohol (1) and proceeds via an oxirane precursor (2) as shown by the reaction scheme below.

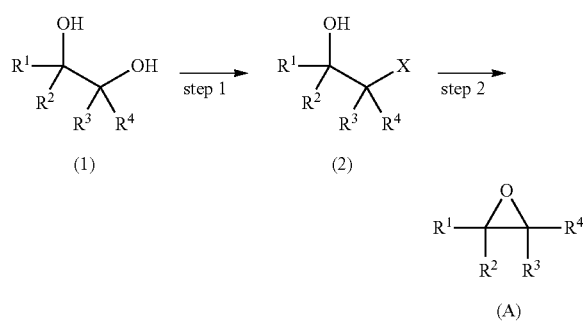

Herein R$^1$ to R$^4$ and X are as defined above.

Step 1 is to use a fluorinated alcohol having formula (1) as the starting reactant and to convert it into an oxirane precursor having formula (2). The fluorinated alcohol (1) as the starting reactant may be synthesized by the method of JP-A 2007-204385 (U.S. Pat. No. 7,868,199).

In an example where the oxirane precursor (2) is a sulfonate of formula (2) wherein X is —OSO$_2$R$^5$ group, the fluorinated alcohol (1) may be reacted with a sulfonylating agent such as p-toluenesulfonyl chloride or p-toluenesulfonic anhydride under basic conditions to form a corresponding sulfonate. The reaction may be performed in a solventless system or in a solvent by sequentially or simultaneously adding the fluorinated alcohol (1), the sulfonylating agent, and an aqueous solution of an organic or inorganic base, and optionally cooling or heating. Suitable solvents include methylene chloride, acetonitrile, toluene, xylene, hexane, tetrahydrofuran, and diisopropyl ether. Suitable organic bases include triethylamine, pyridine and 4-dimethylaminopyridine, and suitable inorganic bases include sodium hydroxide, potassium hydroxide and potassium carbonate.

Although an amount of the sulfonylating agent used varies with conditions, the amount is desirably 1.0 to 1.5 moles, more desirably 1.0 to 1.1 moles per mole of fluorinated alcohol (1). Although an amount of the base also varies with conditions because the base itself may sometimes serve as the solvent, the amount is desirably 1.0 to 20 moles per mole of fluorinated alcohol (1). The reaction is preferably performed and completed at a temperature of 0° C. to 40° C., more preferably 0° C. to 25° C. At temperatures outside the range, the yield may be reduced because polymerization may take place at the same time as formation of 2,2-bis(fluoroalkyl) oxirane (A) during long term heating, or sulfonylation of both hydroxyl groups on the fluorinated alcohol (1) may take place to form more a by-product. It is desirable from the yield aspect to determine a reaction time by monitoring the reaction until completion by gas chromatography (GC) or silica gel thin layer chromatography (TLC). The reaction time is generally 0.5 to 96 hours. The oxirane precursor (2) may be recovered from the reaction mixture by ordinary post-treatment such as aqueous work-up or filtration and purified by a standard technique such as distillation, chromatography or recrystallization. If the compound has a fully high purity, it may be used in the subsequent step without purification, or the reaction solution may be continuously fed to the subsequent step.

In an example where the oxirane precursor (2) is a chloride or bromide of formula (2) wherein leaving group X is chlorine or bromine, the fluorinated alcohol (1) may be reacted with a chlorinating or brominating agent. Exemplary chlorinating agents include thionyl chloride, phosphorus oxychloride, and oxalyl chloride and exemplary brominating agents include phosphorus tribromide and phosphorus pentabromide. The remaining conditions may be similar to the conditions employed for the sulfonylating agent.

As described above, any suitable group may be selected as leaving group X in the reaction to form the oxirane precursor (2) from the fluorinated alcohol (1). Preferably X is a sulfonate group because the precursor is obtained in crystal form which is easy to handle. In the case of chloride or bromide, some chloride or bromide precursors are highly volatile or low boiling liquids which are difficult to handle during purification and storage.

Step 2 is a ring-closing reaction of the oxirane precursor (2) under basic conditions to form 2,2-bis(fluoroalkyl)oxirane (A). The reaction may be readily performed by well-known techniques, for example, in a solventless system or in a solvent by sequentially or simultaneously adding the oxirane precursor (2) and an aqueous solution of an inorganic base, and optionally cooling or heating. Suitable solvents include toluene, xylene, hexane, tetrahydrofuran, and diisopropyl ether. Suitable inorganic bases include sodium hydroxide, potassium hydroxide and potassium carbonate.

Although an amount of the base used varies with conditions, the amount is desirably 1.0 to 1.5 moles, more desirably 1.0 to 1.1 moles per mole of oxirane precursor (2). The reaction is preferably performed and completed at a temperature of 0° C. to 40° C., more preferably 0° C. to 25° C. It is desirable from the yield aspect to determine a reaction time by monitoring the reaction until completion by gas chromatography (GC) or silica gel thin layer chromatography (TLC). The reaction time is generally 0.5 to 12 hours. Outside the range, for example, polymerization of 2,2-bis(fluoroalkyl) oxirane (A) may take place during long-term heating, or side reactions such as hydrolysis of 2,2-bis(fluoroalkyl)oxirane (A) or the residual oxirane precursor (2) may take place during long-term stirring, resulting in a reduced yield. At the end of reaction, the product may be purified by distillation or the like, if desired.

The 2,2-bis(fluoroalkyl)oxirane (A) resulting from the reaction of Step 2 is a water-immiscible oily compound. Thus, when the reaction is performed in an aqueous solution of inorganic base without using a solvent, the 2,2-bis(fluoroalkyl)oxirane (A) of sufficient purity can be separated from the aqueous layer. The possibility of isolation without a need for purification such as by distillation indicates a very efficient process.

Next described is the preparation of an onium salt photoacid generator using the 2,2-bis(fluoroalkyl)oxirane (A) as the starting reactant. As to the preparation of an onium salt photoacid generator using a 2,2-bis(fluoroalkyl)oxirane as the starting reactant, Patent Document 4 (JP-A 2010-215608) describes the preparation of triphenylsulfonium 2-hydroxy-3,3,3-trifluoromethyl-2-trifluoromethylpropanesulfonate and derivatives thereof. The method of the invention is characterized in that subsequent to the preparation of 2,2-bis (fluoroalkyl)oxirane (A) mentioned just above, an onium salt photoacid generator is prepared according to the procedure of Patent Document 4.

The second embodiment is a method for preparing an onium salt photoacid generator having the general formula (4a) or (4b), which starts with the 2,2-bis(fluoroalkyl)oxirane (A) resulting from the method of the first embodiment and proceeds via a sulfonic acid salt compound having the general formula (3).

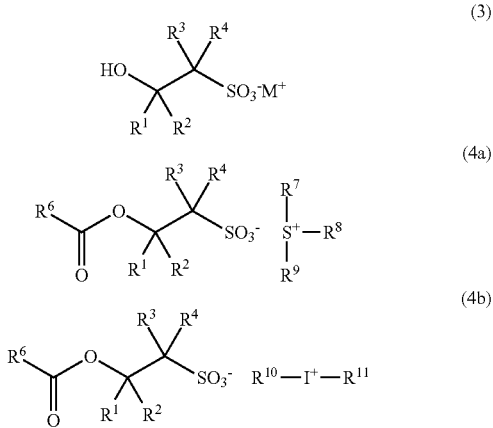

Herein $R^1$ to $R^4$ are as defined above. $R^6$ is a $C_1$-$C_{50}$ straight, branched or cyclic monovalent hydrocarbon group which may contain a heteroatom. M is a cation species. $R^7$, $R^8$ and $R^9$ are each independently a $C_1$-$C_{10}$ straight or branched alkyl, alkenyl or oxoalkenyl group which may contain a fluorine atom, hydroxyl group or ether bond, or a substituted or unsubstituted $C_6$-$C_{18}$ aryl, aralkyl or aryloxoalkyl group, or any two or more of $R^7$, $R^8$ and $R^9$ may bond together to form a ring with the sulfur atom. $R^{10}$ and $R^{11}$ are each independently a substituted or unsubstituted $C_6$-$C_{18}$ aryl, aralkyl or aryloxoalkyl group, or $R^{10}$ and $R^{11}$ may bond together to form a ring with the iodine atom.

Examples of the cation M in the sulfonic acid salt compound of formula (3) include Li, Na, K, $Mg^{1/2}$, $Ca^{1/2}$, substituted or unsubstituted ammonium, sulfonium, and iodonium.

Now the preparation method is described in detail by referring to the synthesis of a sulfonium salt compound having formula (4a). First, the 2,2-bis(fluoroalkyl)oxirane having formula (A) is reacted with a sulfur compound such as sulfite or hydrogensulfite to synthesize a sulfonic acid salt compound having formula (3). In this step, the sulfur compound as one reagent may be selected from many such compounds although sodium hydrogensulfite is best suited because of low cost and ease of handling. An amount of the sulfur compound used is preferably 1.0 to 5.0 moles, more preferably 1.0 to 3.0 moles per mole of the oxirane (A). The reaction temperature is preferably 10 to 40° C., more preferably 20 to 40° C. The reaction time is preferably 4 to 24 hours. The reaction may be performed in water or an alcohol solvent such as methanol, ethanol or 1-propanol, alone or in admixture. Preferably water is used alone.

Next, the sulfonic acid salt compound (3) is subjected to ion exchange with a sulfonium salt such as sulfonium halide to synthesize a sulfonium salt compound having the general formula (5a).

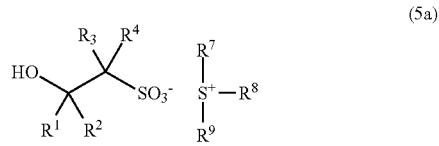

Herein $R^1$ to $R^4$ and $R^7$ to $R^9$ are as defined above. With respect to the ion exchange reaction, reference may be made to JP-A 2007-145797. For example, the desired sulfonium salt compound (5a) can be synthesized and recovered by reacting sulfonic acid salt compound (3) with sulfonium halide in a two-layer system of dichloromethane and water, removing the water layer, and concentrating the organic solvent layer. Ion exchange reaction may be performed after the sulfonic acid salt compound (3) is isolated. Alternatively, the sulfonic acid salt compound (3) may be kept as the crude product and subjected to ion exchange reaction.

Subsequently, the resulting sulfonium salt compound (5a) is acylated to form a sulfonium salt compound having formula (4a). With respect to the acylation reaction, reference may be made to Patent Document 4 (JP-A 2010-215608). Specifically, reaction may be performed in an organic solvent such as dichloromethane, acetonitrile, or tetrahydrofuran using an acylating agent such as carboxylic acid chloride or carboxylic anhydride and an organic base such as triethylamine, pyridine or 4-dimethylaminopyridine.

The sulfonium salt used for ion exchange may be a salt having the formula (6a):

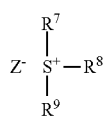

(6a)

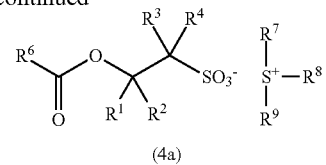

(4a)

wherein $R^7$ to $R^9$ are as defined above, and Z is an anion such as halogen atom.

An amount of the sulfonium salt used is preferably 0.5 to 3.0 moles, more preferably 0.9 to 1.1 moles per mole of the compound (3). The reaction temperature is preferably 0 to 80° C., more preferably 10 to 30° C. The reaction time is preferably 5 minutes to 1 hour. The reaction may be performed in a solvent which is an organic solvent such as dichloromethane, ethyl acetate, methyl isobutyl ketone, methanol, ethanol or acetonitrile, alone or in admixture with water.

An amount of the acylating agent used in the acylation reaction is preferably 1.0 to 10.0 moles, more preferably 1.0 to 2.0 moles per mole of the compound (3). An amount of the organic base used is preferably 1.0 to 20 moles, more preferably 1.0 to 5.0 moles. The reaction temperature is preferably 0 to 80° C., more preferably 10 to 30° C. The reaction time is preferably 0.5 to 20 hours. The reaction may be performed in an organic solvent such as dichloromethane, toluene, hexane, diethyl ether, tetrahydrofuran or acetonitrile.

In an alternative embodiment wherein the sulfonic acid salt compound having formula (3) is a quaternary ammonium salt which is highly soluble in an organic solvent, corresponding to formula (3) wherein M is a substituted or unsubstituted ammonium, once the compound (3) is isolated, acylation reaction is performed, followed by ion exchange with a sulfonium salt such as sulfonium halide.

The process of preparing sulfonium salt compound (4a) is illustrated by the following scheme. The scheme refers to sodium hydrogensulfite as a typical sulfur compound (selected from sulfites and hydrogensulfites) used in the first step although the sulfur compound is not limited thereto.

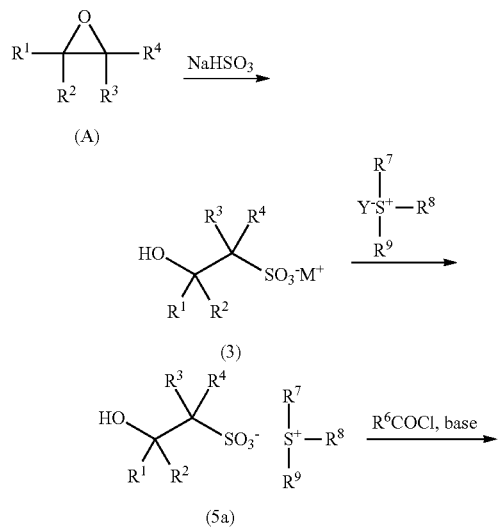

Herein $R^1$ to $R^9$ are as defined above, and Y is an anion such as iodine, bromine or chlorine atom, or $CH_3OSO_3$.

Examples of substituent groups $R^7$, $R^8$ and $R^9$ on the sulfonium cation in formula (4a) include alkyl groups such as methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl; alkenyl groups such as vinyl, allyl, propenyl, butenyl, hexenyl, and cyclohexenyl; oxoalkyl groups such as 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl; aryl groups such as phenyl, naphthyl, thienyl, 4-hydroxyphenyl, 4-fluorophenyl, alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl, alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl, alkylnaphthyl groups such as methylnaphthyl and ethylnaphthyl, alkoxynaphthyl groups such as methoxynaphthyl and ethoxynaphthyl, dialkylnaphthyl groups such as dimethylnaphthyl and diethylnaphthyl, dialkoxynaphthyl groups such as dimethoxynaphthyl and diethoxynaphthyl; aralkyl groups such as benzyl, 1-phenylethyl, and 2-phenylethyl; aryloxoalkyl groups, typically 2-aryl-2-oxoethyl such as 2-phenyl-2-oxoethyl, 2-(1-naphthyl)-2-oxoethyl, and 2-(2-naphthyl)-2-oxoethyl. When any two or more of $R^7$, $R^8$ and $R^9$ bond together to form a ring with the sulfur atom, suitable groups to form the cyclic structure include divalent organic groups such as 1,4-butylene and 3-oxa-1,5-pentylene. Examples of the cyclic structure they form with the sulfur atom include tetrahydrothiophene, thiophene, benzothiophene, dibenzothiophene, and phenoxathiine. Other suitable substituent groups include aryl groups having a polymerizable substituent such as acryloyloxy or methacryloyloxy, suitable examples of which include 4-acryloyloxyphenyl, 4-methacryloyloxyphenyl, 4-acryloyloxy-3,5-dimethylphenyl, 4-methacryloyloxy-3,5-dimethylphenyl, 4-vinyloxyphenyl, and 4-vinylphenyl.

Examples of the sulfonium cation include triphenylsulfonium, S-phenyldibenzothiophenium, 10-phenylphenoxathiinium, 4-fluorophenyldiphenylsulfonium, 4-hydroxyphenyldiphenylsulfonium, bis(4-hydroxyphenyl)phenylsulfonium, tris(4-hydroxyphenyl)sulfonium, tris(4-fluorophenyl)sulfonium, 4-tert-butoxyphenyldiphenylsulfonium, bis(4-tert-butoxyphenyl)phenylsulfonium, tris(4-tert-butoxyphenyl)sulfonium, 3-tert-butoxyphenyldiphenylsulfonium, bis(3-tert-butoxyphenyl)phenylsulfonium, tris(3-tert-butoxyphenyl)sulfonium, 3,4-di-tert-butoxyphenyldiphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, (4-hydroxy-3,5-dimethylphenyl)diphenylsulfonium, (4-n-hexyloxy-3,5-dimethylphenyl)diphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-hydroxynaphthyl-1-thiacyclopentanium, 4-(2,2,2-trifluoroethoxy)naphthyl-1-thiacyclopentanium, 4-methoxynaphthyl-1-thiacyclopentanium, and 2-methoxynaphthyl-1-thiacyclopentanium. Preferred cations are triphenylsulfonium, 4-tert-butylphenyldiphenylsulfonium, 4-tert-butoxyphenyldiphenylsulfonium, tris(4-tert-butylphenyl)sulfonium, and 4-tert-butoxycarbonylmethyloxyphenyldiphenylsulfonium. Also included are 4-methacryloyloxyphenyldiphenylsulfonium, 4-acryloyloxyphenyldiphenylsulfonium, 4-methacryloyloxyphenyldimethylsulfonium, 4-acryloyloxyphenyldimethylsulfonium, (4-methacryloyloxy-3,5-dimethylphenyl)diphenylsulfonium, and (4-acryloyloxy-3,5-dimethylphenyl)diphenylsulfonium. With respect to these polymerizable sulfonium cations, reference may be made to JP-A H04-230645 and JP-A 2005-84365. The polymerizable sulfonium salts may be used as a monomer in forming a higher molecular weight compound.

While examples of the sulfonium salt compound (4a) are enumerated above, an iodonium salt compound having formula (4b) may be similarly obtained by effecting ion exchange reaction on the sulfonic acid salt compound having formula (3) and an iodonium salt such as iodonium halide and acylation reaction.

The iodonium salt used for ion exchange may be a salt having the formula (6b):

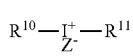
(6b)

wherein $R^{10}$, $R^{11}$ and Z are as defined above.

An amount of the iodonium salt used is preferably 0.5 to 3.0 moles, more preferably 0.9 to 1.1 moles per mole of the compound (3). Other reaction conditions are the same as above.

The substituent groups $R^{10}$ and $R^{11}$ on the iodonium cation in the iodonium salt compound having formula (4b) are as exemplified for $R^7$, $R^8$ and $R^9$. Suitable iodonium cations include diphenyliodonium, bis(4-methylphenyl)iodonium, bis(4-(1,1-dimethylethyl)phenyl)iodonium, bis(4-(1,1-dimethylpropyl)phenyl)iodonium, and (4-(1,1-dimethylethoxy)phenyl)phenyliodonium.

The sulfonic acid salt compound having formula (3), and the sulfonium and iodonium salt compounds having formulae (4a) and (4b) can be synthesized without complex steps and expensive reactants, and the substituent group structure may be altered over a wide range in accordance with a particular application. According to the invention, the 2,2-bis(fluoroalkyl)oxiranes from which these salt compounds are prepared can be prepared at low costs and in high yields without forming toxic by-products. The inventive method enables industrially advantageous manufacture of onium salt compounds.

EXAMPLE

Examples of the invention are given below by way of illustration and not by way of limitation.

Example 1

Synthesis of 2,2-bis(trifluoromethyl)oxirane 2,2-Bis(trifluoromethyl)oxirane was synthesized by the following procedure.

REFERENCE SYNTHESIS EXAMPLE

Synthesis of 3,3,3-trifluoro-2-trifluoromethyl-1,2-propane diol

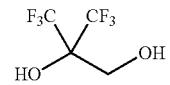

Synthesis was carried out in accordance with the procedure described in U.S. Pat. No. 7,868,199. In a nitrogen atmosphere, 84 g of sodium boron hydride, 1,450 g of diisopropyl ether (IPE), 2,000 g of water and 1.7 g of 25 wt % NaOH aqueous solution were ice cooled, to which 500 g of methyl 3,3,3-trifluoro-2-hydroxy-2-(trifluoromethyl)propanoate was added dropwise. Stirring was continued for 24 hours at room temperature. Under ice cooling, 444 g of 20 wt % hydrochloric acid aqueous solution was added dropwise to quench the reaction. After the water layer was removed, the organic layer was washed with water and concentrated at 50° C. and a slightly reduced pressure of 6.7 kPa, obtaining 682 g of a 61 wt % IPE solution of 3,3,3-trifluoro-2-trifluoromethyl-1,2-propane diol (yield 95%). The compound was used in the subsequent reaction without further purification.

$^1$H-NMR (300 MHz in DMSO-$d_6$): δ=3.79 (2H, s), 5.58 (1H, br), 7.64 (1H, br) ppm

Synthesis Example 1-1

Synthesis of 3,3,3-trifluoro-1-(p-toluenesulfonyloxy)-2-trifluoromethylpropan-2-ol

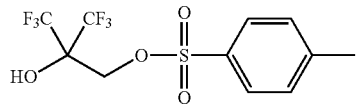 [SMILES: Cc1ccc(S(=O)(=O)OCC(O)(C(F)(F)F)C(F)(F)F)cc1]

Under ice cooling, a solution of 54 g of p-toluene sulfonate in 140 g of pyridine was added dropwise to a mixture of 93 g of the 61 wt % IPE solution of 3,3,3-trifluoro-2-trifluoromethyl-1,2-propane diol prepared in Reference Synthesis Example and 140 g of pyridine. Stirring was continued for 48 hours at room temperature. The reaction solution was ice cooled and poured into a mixture of 678 g of 20 wt % hydrochloric acid aqueous solution and 100 g of ice to quench the reaction. Toluene, 500 g, was added to the reaction solution, which was separated into layers. The organic layer was washed with water, concentrated, and recrystallized from heptane, obtaining 74 g of 3,3,3-trifluoro-1-(p-toluene-sulfonyloxy)-2-trifluoromethylpropan-2-ol (yield 74%).

IR (D-ATR): ν=3374, 1595, 1492, 1460, 1421, 1361, 1317, 1275, 1249, 1229, 1218, 1190, 1175, 1163, 1094, 1018, 971, 926, 825, 812, 792, 765, 719, 705, 662, 554 cm$^{-1}$ $^1$H-NMR (500 MHz in DMSO-d$_6$): δ=2.43 (3H, s), 4.31 (2H, s), 7.51 (2H, m), 7.82 (2H, m), 8.69 (1H, s) ppm Synthesis Example 1-2

Synthesis of 2,2-bis(trifluoromethyl)oxirane

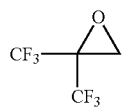

Under ice cooling, 32 g of 25 wt % sodium hydroxide aqueous solution was added dropwise to a suspension of 70 g of 3,3,3-trifluoro-1-(p-toluenesulfonyloxy)-2-trifluoro-methylpropan-2-ol obtained in Synthesis Example 1-1 in 140 g of water. Stirring was continued for one hour under ice cooling, after which the reaction solution was transferred into a separatory funnel where it separated into two layers. The lower layer was taken out, obtaining 33 g of 2,2-bis(trifluoromethyl)oxirane (yield 91%).

IR (D-ATR): ν=1402, 1366, 1196, 1149, 1060, 996, 872, 759, 689, 637 cm$^{-1}$ $^1$H-NMR (500 MHz in CDCl$_3$): δ=3.28 (2H, s) ppm Example 2

Synthesis of triphenylsulfonium 2-(adamantane-1-carbonyl-oxy)-3,3,3-trifluoro-2-trifluoromethylpropane-1-sulfonate The method of the invention was used to synthesize triphenylsulfonium 2-adamantyloxy-3,3,3-trifluoromethyl-2-trifluoromethylpropanesulfonate, which was a sulfonium salt compound useful as a photoacid generator in the photolithography.

Synthesis Example 2-1

Synthesis of triphenylsulfonium 3,3,3-trifluoro-2-hydroxy-2-trifluoromethylpropane-1-sulfonate

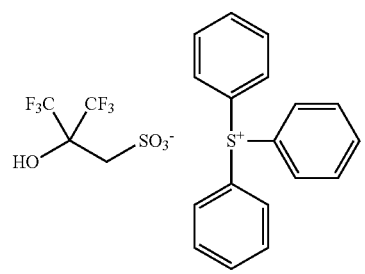

Using the 2,2-bis(trifluoromethyl)oxirane prepared in Synthesis Example 1-2, synthesis was carried out in accordance with the procedure described in US 20100209827. A mixture of 30 g of 2,2-bis(trifluoromethyl)oxirane, 26 g of sodium hydrogensulfite, and 120 g of water was stirred at 40° C. for 10 hours, obtaining an aqueous solution of sodium 3,3,3-trifluoro-2-hydroxy-2-trifluoromethylpropane-1-sulfonate. Subsequently, 34 g of an aqueous solution of 2,000 g/mol of triphenylsulfonium chloride and 400 g of methylene chloride were added to the aqueous solution, which was stirred for 4 hours at room temperature. At the end of stirring, the organic layer was taken out, washed with water, and concentrated under reduced pressure. The concentrate was combined with methyl isobutyl ketone and concentrated again under reduced pressure to distill off the residual water. To the residue, diisopropyl ether was added for recrystallization, obtaining 74 g of triphenylsulfonium 3,3,3-trifluoro-2-hydroxy-2-trifluoromethylpropane-1-sulfonate (yield 85%).

IR (KBr): ν=3060, 1476, 1448, 1329, 1253, 1227, 1191, 1145, 1029, 1011, 968, 780, 760, 749, 685, 497 cm$^{-1}$ $^1$H-NMR (300 MHz in DMSO-d$_6$): δ=1.60-1.94 (15H, m), 3.55 (2H, s), 7.76-7.89 (15H, m) ppm Synthesis Example 2-2

Synthesis of triphenylsulfonium 2-(adamantane-1-carbonyl-oxy)-3,3,3-trifluoro-2-trifluoromethylpropane-1-sulfonate The triphenylsulfonium 3,3,3-trifluoro-2-hydroxy-2-trifluoromethylpropane-1-sulfonate prepared in Synthesis Example 2-1, 70 g, was mixed with 16.2 g of triethylamine, 3.3 g of 4-dimethylaminopyridine, and 250 g of methylene chloride. 71 g of a 44 wt % methylene chloride solution of adamantane-1-carbonyl chloride was added to the mixture, which was stirred for 2 hours at room temperature. Then 175 g of 5 wt % hydrochloric acid aqueous solution was added to quench the reaction. The organic layer was taken out, washed with water, and concentrated under reduced pressure. The concentrate was combined with methyl isobutyl ketone and concentrated again under reduced pressure to distill off the residual water. To the residue, diisopropyl ether was added for recrystallization, obtaining 77 g of triphenylsulfonium 2-(adamantane-1-carbonyloxy)-3,3,3-trifluoro-2-trifluoromethylpropane-1-sulfonate (yield 85%).

IR (KBr): ν=3443, 2908, 2853, 1760, 1477, 1448, 1330, 1297, 1253, 1239, 1220, 1197, 1127, 1062, 1041, 1018, 969, 750, 684, 616, 595, 517, 501 cm$^{-1}$ $^1$H-NMR (500 MHz in CDCl$_3$): δ=3.28 (2H, s) ppm In Table 1, the method of preparing 2,2-bis(fluoroalkyl) oxirane in Example 1 according to the invention is compared with the prior art, Prior Art Example 1 (U.S. Pat. No. 6,653,419) and Prior Art Example 2 (US 20080177097).

TABLE 1

|  | Example 1 | Prior Art Example 1 | Prior Art Example 2 |
| --- | --- | --- | --- |
| Reactant structure | (AA) | (B) | (B) |
| Reactant's boiling point (° C.) | used in solution form (bp 138° C.) | 14.5° C. | 14.5° C. |
| By-product | nil | (C) | nil |

$F_3C$ $CF_3$
HO $\diagup$ OH (AA)

TABLE 1-continued

| | Example 1 | Prior Art Example 1 | Prior Art Example 2 |
|---|---|---|---|

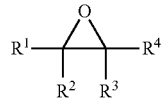

(B)  (C)

As understood from Table 1, the method of the invention is successful in preparing 2,2-bis(trifluoromethyl)oxirane using the reactant (AA) having a high boiling point sufficient to eliminate any volatilization loss during normal handling and the potential risk of workers inhaling the vapor. Many intermediates resulting from the reactant (AA) are available in crystal form which is easy to handle. Even when cooling is necessary in a certain step, the method of the invention can be implemented in safety as long as cooling to the level of ice cooling (around 0° C.) is possible. While toxic hexafluoroacetone (C) forms as a by-product of oxidation of fluoroolefin (B) in Prior Art Example 1, no toxic compounds including hexafluoroacetone (C) were found in the method of the invention.

The method of the invention is successful in preparing 2,2-bis(trifluoroalkyl)oxiranes in a simple and safe manner and advantageous in efficient preparation of photoacid generators.

Japanese Patent Application No. 2011-144456 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for preparing a 2,2-bis(fluoroalkyl)oxirane of formula (A), comprising:

reacting a fluorinated alcohol of formula (1) with a chlorinating agent, brominating agent or sulfonylating agent under basic conditions to form an oxirane precursor of formula (2), and subjecting the oxirane precursor to ring closure under basic conditions,

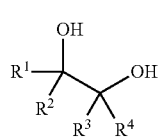

(1)

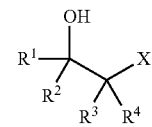

(2)

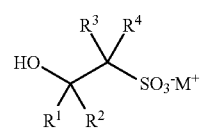

(A)

wherein
R$^1$ and R$^2$ are each independently a C$_1$-C$_6$ straight or branched fluoroalkyl group,
R$^3$ and R$^4$ are each independently hydrogen or a C$_1$-C$_{15}$ straight, branched or cyclic monovalent hydrocarbon group, or R$^3$ and R$^4$ may bond together to form a ring with the carbon atom to which they are attached,
X is chlorine, bromine or —OSO$_2$R$^5$ group, and
R$^5$ is a C$_1$-C$_{15}$ straight, branched or cyclic alkyl group or an aryl group which may comprise a heteroatom.

2. A method for preparing a sulfonic acid salt compound of formula (3), comprising:
reacting a 2,2-bis(fluoroalkyl)oxirane of formula (A) prepared by the method of claim 1 with a sulfur compound, (3)

HO—C(R$^1$)(R$^2$)—C(R$^3$)(R$^4$)—SO$_3^-$M$^+$ wherein
R$^1$ and R$^2$ are each independently a C$_1$-C$_6$ straight or branched fluoroalkyl group,
R$^3$ and R$^4$ are each independently hydrogen or a C$_1$-C$_{15}$ straight, branched or cyclic monovalent hydrocarbon group, or R$^3$ and R$^4$ may bond together to form a ring with the carbon atom to which they are attached, and
M is a cation.

3. A method for preparing a sulfonium or iodonium salt compound of formula (4a) or (4b), comprising:
subjecting a sulfonic acid salt compound of formula (3) prepared by the method of claim 2 to ion exchange reaction with a sulfonium salt or iodonium salt and acylation reaction,

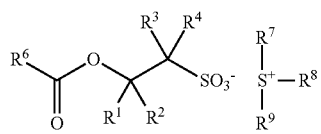

(4a)

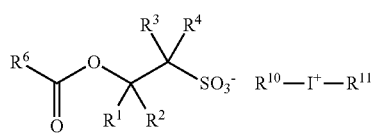

(4b)

wherein
R$^1$ and R$^2$ are each independently a C$_1$-C$_6$ straight or branched fluoroalkyl group,
R$^3$ and R$^4$ are each independently hydrogen or a C$_1$-C$_{15}$ straight, branched or cyclic monovalent hydrocarbon group, or R$^3$ and R$^4$ may bond together to form a ring with the carbon atom to which they are attached, $R^6$ is a $C_1$-$C_{50}$ straight, branched or cyclic monovalent hydrocarbon group which may comprise a heteroatom, $R^7$, $R^8$ and $R^9$ are each independently a $C_1$-$C_{10}$ straight or branched alkyl, alkenyl or oxoalkenyl group which may comprise a fluorine atom, hydroxyl group, ether bond, substituted or unsubstituted $C_6$-$C_{18}$ aryl, aralkyl or aryloxoalkyl group, or any two or more of $R^7$, $R^8$ and $R^9$ may bond together to form a ring with the sulfur atom, and $R^{10}$ and $R^{11}$ are each independently a substituted or unsubstituted $C_6$-$C_{18}$ aryl, aralkyl or aryloxoalkyl group, or $R^{10}$ and $R^{11}$ may bond together to form a ring with the iodine atom.

* * * * *